(12) United States Patent
Luan et al.

(10) Patent No.: US 9,541,541 B2
(45) Date of Patent: *Jan. 10, 2017

(54) NANOPORE DEVICE FOR DRUG-LIKE MOLECULE SCREENING OR LEAD OPTIMIZATION TO A TARGETED PROTEIN

(71) Applicant: GLOBALFOUNDRIES INC., Grand Cayman (KY)

(72) Inventors: Binquan Luan, Chappaqua, NY (US); Ruhong Zhou, Stormville, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 689 days.

This patent is subject to a terminal disclaimer.

(21) Appl. No.: 13/873,854

(22) Filed: Apr. 30, 2013

(65) Prior Publication Data

US 2014/0318962 A1    Oct. 30, 2014

(51) Int. Cl.
*G01N 27/447* (2006.01)
*G01N 33/487* (2006.01)
*G01N 33/68* (2006.01)
*B82Y 30/00* (2011.01)

(52) U.S. Cl.
CPC .... *G01N 33/48721* (2013.01); *G01N 33/6872* (2013.01); *B82Y 30/00* (2013.01)

(58) Field of Classification Search
CPC ............... G01N 27/44791; G01N 27/4473; G01N 27/447; G01N 33/48721; Y10S 977/852; Y10S 977/733; Y10S 977/72; Y10S 977/721; B82Y 5/00; B82Y 15/00
See application file for complete search history.

(56) References Cited

U.S. PATENT DOCUMENTS

| | | | |
|---|---|---|---|
| 4,537,973 A | 8/1985 | Takahashi et al. |
| 7,005,264 B2 | 2/2006 | Su et al. |
| 7,468,271 B2 | 12/2008 | Golovchenko et al. |
| 7,846,738 B2 | 12/2010 | Golovchenko et al. |
| 7,993,524 B2 | 8/2011 | Ratto et al. |
| 8,246,995 B2 | 8/2012 | Dai et al. |

(Continued)

FOREIGN PATENT DOCUMENTS

WO    WO2010042514 A1    4/2010

OTHER PUBLICATIONS

Comer et al., Electrophoresis 2012, 33, 3466-3479.*

(Continued)

*Primary Examiner* — Luan Van
*Assistant Examiner* — Gurpreet Kaur
(74) *Attorney, Agent, or Firm* — Michael LeStrange; Hoffman Warnick, LLC (57) ABSTRACT

A nanosensor for detecting molecule characteristics includes a membrane having an opening configured to permit a charged molecule to pass but to block a protein molecule attached to a ligand connecting to the charged molecule, the opening being filled with an electrolytic solution. An electric field generator is configured to generate an electric field relative to the opening to drive the charged molecule through the opening. A sensor circuit is coupled to the electric field generator to sense current changes due to charged molecules passing into the opening. The current changes are employed to trigger a bias field increase to cause separation between the ligand and the protein to infer an interaction strength.

7 Claims, 6 Drawing Sheets

(56) References Cited

U.S. PATENT DOCUMENTS

| | | | |
|---|---|---|---|
| 2006/0246438 A1* | 11/2006 | McCall | B82Y 5/00 |
| | | | 435/6.12 |
| 2008/0008760 A1 | 1/2008 | Bianco et al. | |
| 2008/0171316 A1* | 7/2008 | Golovchenko | C12Q 1/6869 |
| | | | 435/6.11 |
| 2008/0193490 A1 | 8/2008 | Hirsch et al. | |
| 2012/0219985 A1 | 8/2012 | Yoon et al. | |
| 2012/0261261 A1 | 10/2012 | Huber et al. | |

OTHER PUBLICATIONS

Ge, C., et al. "Binding of Blood Proteins to Carbon Nanotubes Reduces Cytotoxicity" PNAS, vol. 108, No. 41. Oct. 2011. pp. 16968-16973.

King, G., et al. "Probing Nanotube-Nanopore Interactions" Physical Review Letters, vol. 95. Nov. 2005. (4 Pages).

Luan, B., et al. "Nanopore-Based Sensors for Detecting Toxicity of a Carbon Nanotube to Proteins" J Phys. Chem. Lett., vol. 3, No. 17. Aug. 2012. pp. 1-15.

Nel, A., et al. "Toxic Potential of Materials At the Nanolevel" Science, vol. 311, No. 5761. Feb. 2006. pp. 622-627.

Porter, A., et al. "Direct Imaging of Single-Walled Carbon Nanotubes in Cells" Nature Nanotechnology, vol. 2. Oct. 2007. pp. 713-717.

Yen, I., et al. "Nucleic Acid Transport Through Carbon Nanotube Membranes" PNAS, vol. 101, No. 33. Aug. 2004. pp. 12177-12182.

Zuo, G., et al. "Plugging Into Proteins: Poisoning Protein Function by a Hydrophobic Nanoparticle" ACS Nano, vol. 4, No. 12. Nov. 2010. pp. 7508-7514.

Luan, B., et al. "Nanopore Sensor for Detecting Molecular Interactions" U.S. Appl. No. 13/873,815, filed Apr. 30, 2013. (27 Pages).

Hall et al., Translocation of Single-Wall Carbon Nanotubes Through Solid-State Nanopores, 11, 2446-2450, 2011.

Zhao et al., Detecting SNPs Using a Synthetic Nanopore, Nano Letters, vol. 7, No. 6, pp. 1680-1685, 2007.

* cited by examiner

NANOPORE DEVICE FOR DRUG-LIKE MOLECULE SCREENING OR LEAD OPTIMIZATION TO A TARGETED PROTEIN

RELATED APPLICATION INFORMATION

This application is related to U.S. patent application Ser. No. 13/873,815 filed currently herewith and incorporated herein by reference in its entirety.

BACKGROUND

Technical Field

The present invention relates to sensors, and more particularly to nanopore sensors and methods for detecting interaction between carbon nanotubes and proteins.

Description of the Related Art

Developing low-cost and high-throughput methods to screen designed drug-like molecules facilitates drug discovery and biomedical research in general. However, current methods of drug screening usually involve tedious sample-preparation and costly biological/chemical experiments.

SUMMARY

A nanosensor for detecting molecule characteristics includes a membrane having an opening configured to permit a charged molecule to pass but to block a protein molecule attached to a ligand connecting to the charged molecule, the opening being filled with an electrolytic solution. An electric field generator is configured to generate an electric field relative to the opening to drive the charged molecule through the opening. A sensor circuit is coupled to the electric field generator to sense current changes due to charged molecules passing into the opening. The current changes are employed to trigger a bias field increase to cause separation between the ligand and the protein to infer an interaction strength.

A nanosensor for detecting molecule characteristics includes a membrane having one or more openings, each opening being configured to permit a charged carbon nanotube to pass but to block a protein molecule attached to a ligand connecting to the carbon nanotube, the one or more openings being filled with an electrolytic solution. An electric field generator is configured to generate an electric field relative to the opening to drive the charged carbon nanotubes through the one or more openings. A sensor circuit is coupled to the electric field generator to sense current changes due to charged carbon nanotubes passing through the one or more openings. The current changes are employed to trigger an increase in the electric field to cause a force of separation between the ligand and the protein molecule at a critical voltage value, the critical voltage value being employed to infer an interaction strength between the ligand and the protein molecule.

A method for detecting molecule characteristics includes generating an electric field across a membrane having an opening to drive a charged molecule through the opening, the charged molecule being connected to a ligand, the ligand being bonded to a protein molecule, the opening being configured to permit the charged molecule to pass but to block the protein molecule attached to the charged particle, the opening being filled with an electrolytic solution; sensing current changes due to the charged molecule passing into or through the opening; biasing the electric field to cause a separation between the ligand and the protein molecule; and correlating a voltage at the separation to measure a characteristic of a protein molecule to ligand interaction.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

In accordance with the present principles, a drug-screening device is provided that employs a physical method with little to no sample preparation. The drug-screening device can provide a low-cost and high-throughput method for screening drugs. A nanopore is employed as a force sensor to detect an affinity between a drug molecule (ligand) and a targeted protein molecule (receptor). The binding affinity of the complex can be derived from measured electric signals. The application of this ultra-sensitive (e.g., for a binding energy of a few $k_BT$ (e.g., 1-10) between the ligand and the protein) screening device could greatly accelerate the process of developing new drugs, particularly for narrow screening and lead optimization.

Screening is a method for scientific experimentation used in drug discovery. Using robotics, data processing and control software, liquid handling devices, and sensitive detectors, screening permits a researcher to quickly conduct millions of chemical, genetic or pharmacological tests. Through this process one can rapidly identify active compounds, antibodies or genes which modulate a particular biomolecular pathway. The results of these experiments provide starting points for drug design and for understanding the interaction or role of a particular biochemical process in biology. Lead optimization is the process of optimizing a drug and bringing a new drug to market once a lead compound has been identified through a drug discovery process. By employing the present principles, narrow screening and lead optimization are improved by reducing the time and resources needed for these and other drug discovery processes.

In one embodiment, a method and device are provided for detecting an affinity of a drug molecule to a targeted protein molecule using a nanopore (a nanometer-sized hole in a thin membrane). The binding affinity of a complex may also be detected using multiple nanopores, a fluidic channel or multiple fluidic channels to screen drug molecules (ligands) to a targeted protein molecule (receptor). A charged carbon nanotube (CNT) is employed to determine the binding affinity; however, the CNT may be replaced with other linear and charged molecules (such as DNA or a nano-wire).

It is to be understood that the present invention will be described in terms of a given illustrative architecture having a nanopore; however, other architectures, structures, materials and process features and steps may be varied within the scope of the present invention.

It will also be understood that when an element such as a layer, region, membrane, etc. is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1:
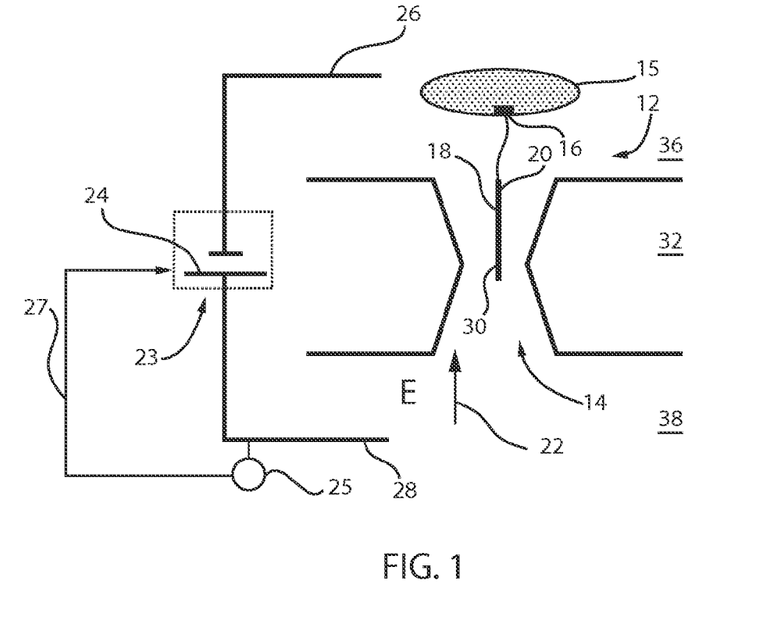
FIG. 1 is a schematic diagram showing a nanopore-based device for drug screening wherein a complex is electrophoretically driven through a nanopore that separates cis. and trans. chambers in accordance with one embodiment.

Referring now to the drawings in which like numerals represent the same or similar elements and initially to FIG. 1, a cross-sectional view shows a sensor device 10 with a complex 12 moving through a nanopore 14. The complex 12 includes a targeted protein molecule 15, a drug molecule 16, and a ligand-functionalized molecule 18 such as a carbon nanotube (CNT) or other charged molecule, e.g., DNA or portion thereof, nanowire, etc.). For illustrative purposes molecule 18 will be references as a CNT 18. A protein ligand is an atom, a molecule or an ion which can bind to a specific site (the binding site) on a protein. Alternative names used to mean a protein ligand are affinity reagents or protein binders. Antibodies are the most widely used protein ligands; however, other molecules such as protein scaffolds, nucleic acids, peptides may also be used.

A first end portion 20 of the CNT 18 is functionalized with charged chemical groups (such as a carboxyl group or amines). The charged CNT 18 allows electrophoretic motion of the complex in a biasing electric field 22. The biasing field 22 is generated by a DC source such as a battery 24 or the like connected across two electrodes 26 and 28. A second end portion 30 of the CNT has a functionalized group that can be further chemically bonded with various test drug-molecules 16, e.g. drug molecules to be tested.

Two fluidic chambers 36, 38 (cis. and trans., respectively) are separated by a membrane 32 and connected via the nanopore 14. The membrane 32 may include, for example, $SiO_2$ or $Si_3N_4$ or any other suitable material. CNT 18 is configured with test drug-molecules 16 and allowed to interact or mix with protein molecules 15 to form a connection. The size of the nanopore 14 (or nanochannel) should be larger than a size of the CNT 18 and smaller than the size of the target protein 15, e.g. 3 nm in diameter.

A sensor circuit 25 is coupled to the electric field generator 23 to sense current changes due to charged carbon nanotubes passing into the opening, and to bias the electric field generator 23 (control or bias the battery 26) through feedback 27 to reach and determine a critical voltage. The critical voltage, in turn, is employed to determine a force of separation between the drug molecule 16 and the protein molecule 15.

The biasing electric field circuit or field generating circuit 23 is applied across the membrane 32, by inserting two electrodes 26, 28 (such as, e.g., Ag/AgCl electrodes connected to the battery 24, other electrode types may also be employed) into cis. (this side) and trans. (the other side) chambers 36, 38, respectively. The biasing voltage can range from about 100 mV to about 1 V.

The fluid chambers 36, 38 are compartments that are configured to store a solution containing test molecules. The solution is electrolytic and may include a 1M solution, although other solution concentrations may be employed. The complex 12 can be prepared by mixing the tested protein molecules with funtionalized CNTs (or other charged molecules) in the electrolyte solution. Funtionalized CNTs include drug molecules or ligands to be tested with the protein.

The sensor circuit 25 is coupled to the circuit 23 to measure changes in current. The sensor 25 may include known devices for accurately measuring transient currents in the circuit 23, such as a patch clamp amplifier. After binding of the test drug-molecule 16 to the targeted protein molecule 15 in an electrolyte of the cis chamber 36, the entire complex 12 is then electrically driven towards and through the nanopore 14.

Figure 2:
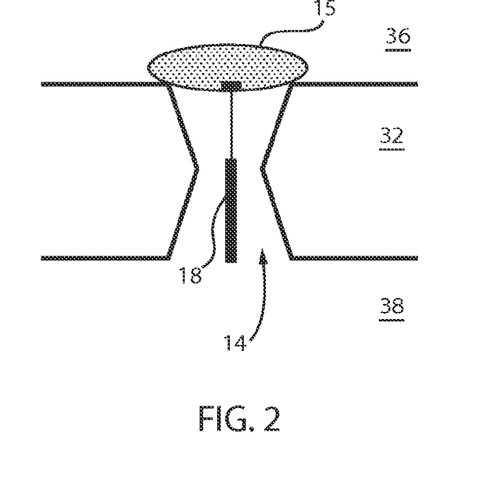
FIG. 2 is a schematic diagram showing the nanopore-based device of FIG. 1 with increased electric field biasing where the complex is physically stuck in the nanopore in accordance with the present principles.

Referring to FIG. 2, in the biasing electric field 22, the charged CNT 18 is electrically driven into the nanopore 14. The nanopore 14 needs to be larger in size than the diameter of the CNT 18 and less than the size of the protein molecule 15. Therefore, during the translocation process, the protein molecule 15 is too large to move through the nanopore 14 and is stuck at the entrance of the nanopore 14.

Figure 3:
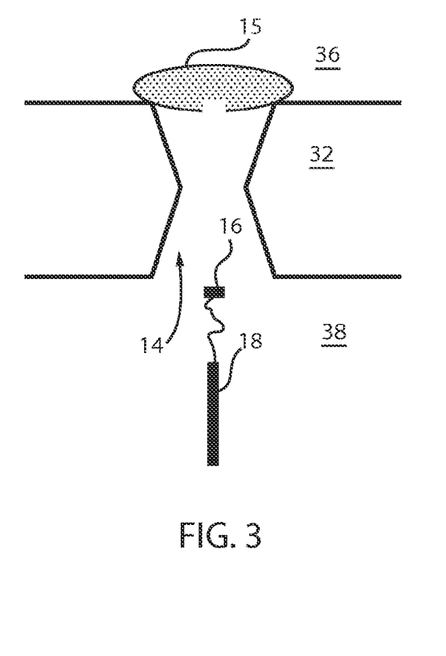
FIG. 3 is a schematic diagram showing the nanopore-based device of FIG. 2, after a rupture between a drug molecule and a targeted protein occurs due to an elevated biasing electric field in accordance with the present principles.

Referring to FIG. 3, when a biasing voltage at a critical value ($V_{cr}$) or higher is achieved, the CNT 18 can be further pulled through the nanopore 14. The interaction strength (thus the binding affinity) between a CNT-connected ligand 16 and the protein molecule 15 can be inferred from the critical value $V_{cr}$ (e.g., the biasing voltage at separation).

Figure 4:
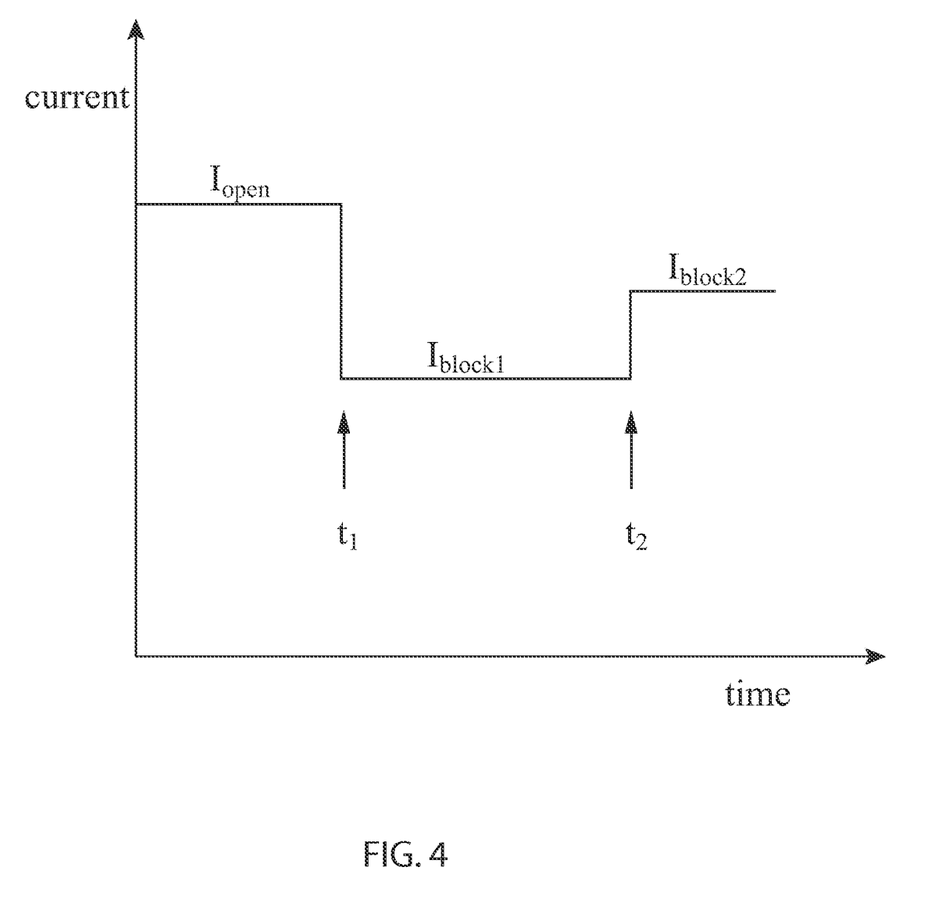
FIG. 4 shows time-dependent ionic-current signals when electrically driving a complex through a nanopore in accordance with one embodiment.

Referring to FIG. 4, the translocation process can be monitored by measuring the ionic current through the nanopore 14. Time-dependent current signals during a translocation/rupture event are illustratively shown in a plot of current (I) versus time (t). At the beginning, the complex is outside the nanopore, and $I_{open}$ is the open-pore current. At the time $t_1$, the complex enters the pore and the ionic current $I_{block1}$ is reduced. This is due to the fact that the complex partially blocks the nanopore. If the biasing voltage is less than the critical value, the current remains constant at $I_{block1}$. At time $t_2$, the biasing voltage is increased to allow a larger pulling force on the CNT. If the biasing voltage is larger than a critical value $V_{cr}$, the complex is pulled apart and the CNT is further driven through the pore, and the pore becomes less blocked. Thus, the ionic current through the pore increases to $I_{block2}$.

Therefore, by monitoring a biasing voltage, it is possible to determine the critical biasing voltage at which a rupture between the CNT and the protein molecule occurs. The rupture force can be estimated using $q_{eff}V_{cr}/d$, where $q_{eff}$ is the effective charge of the CNT after ionic screening in an electrolyte and d is the thickness of a solid-state membrane.

Figure 5:
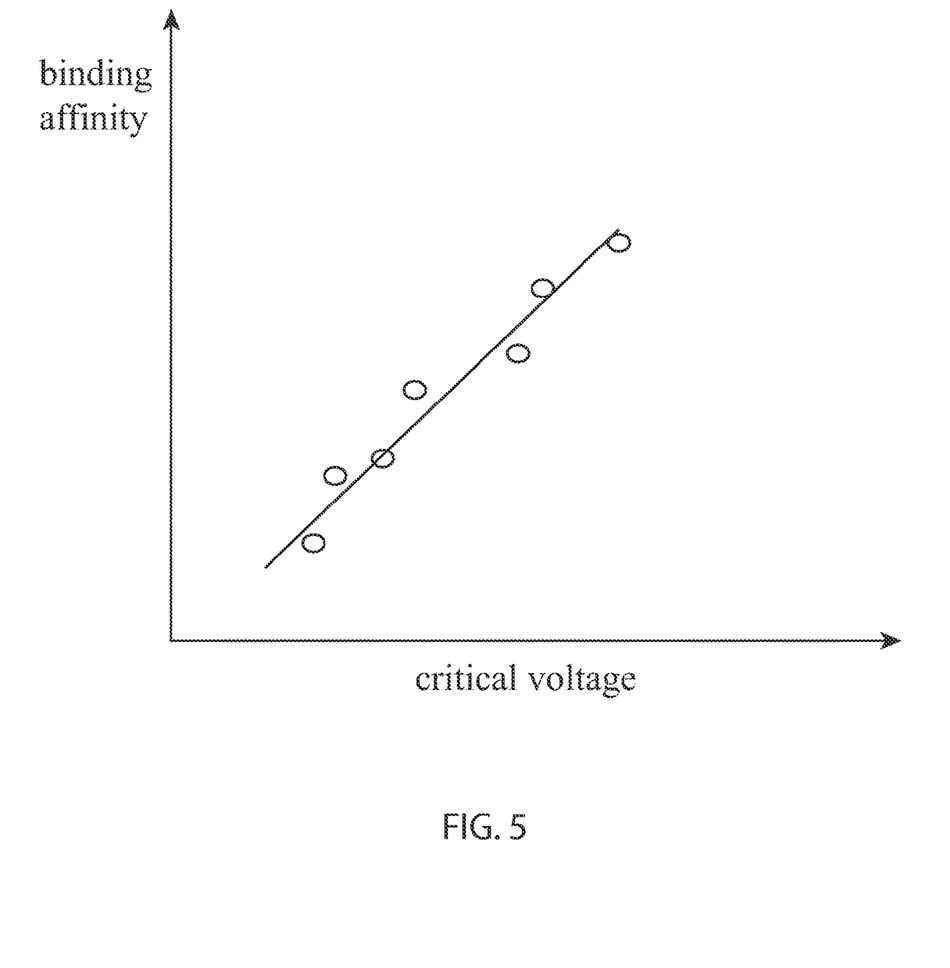
FIG. 5 is an illustrative plot showing binding affinity versus critical voltage for determining separation strength between CNTs and proteins in accordance with the present principles.

Referring to FIG. 5, a plot of binding affinity versus critical voltage illustrates a relation that can be determined experimentally or theoretically. The binding affinity can be inferred from the critical voltage at which the rupture between a CNT and a protein molecule occurs. This provides a high-throughput and low-cost way to determine the interaction between a CNT and a protein molecule. Binding affinity may be employed as one indication of an interaction between a ligand or drug molecule and a protein.

Figure 6:
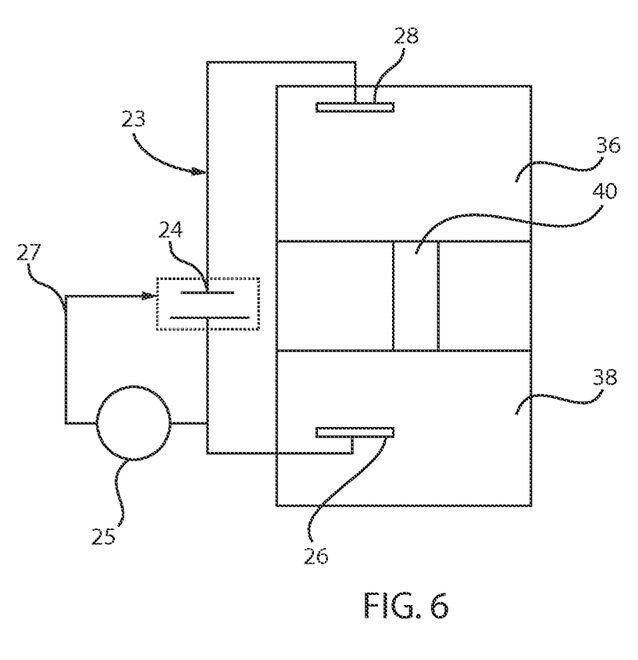
FIG. 6 is a cross-sectional view of a channel based sensor in accordance with another embodiment.

Referring to FIG. 6, another embodiment shows a planar channel 40 employed instead of a nanopore 14. The planar channel 40 is configured to permit the CNT-protein complex to be separated such that the CNT 18 passes into the channel 40 and the protein molecule 15 (not shown) does not. An electric field is applied as before with the battery 24 and electrodes 26, 28 being employed to provide the field and to measure the current changes due to the CNT-protein complex as before. The planar channel 40 has a channel constriction size being less than that of the protein molecule 15.

Figure 7:
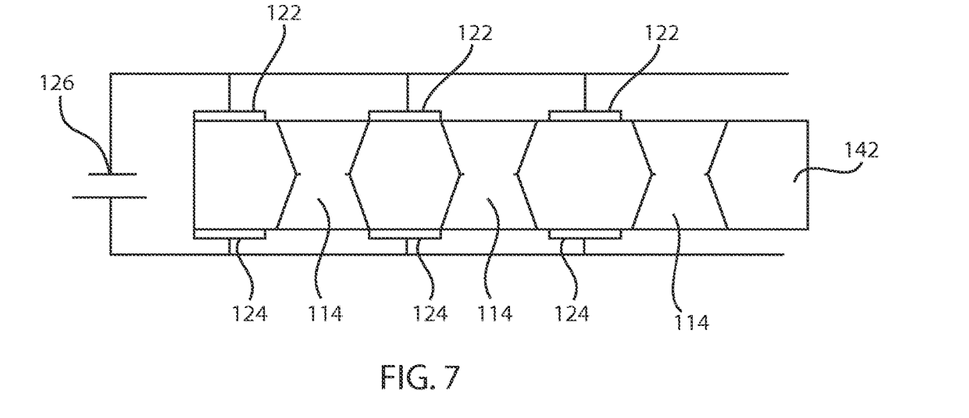
FIG. 7 is a cross-sectional view of a multiple nanopore sensor in accordance with another embodiment.

Referring to FIG. 7, in another embodiment, multiple nanopores 114 may be employed through a same membrane 142. The nanopores 114 function as parallel paths to process CNT-protein complexes more rapidly. A battery 126 and electrodes 122, 124 are dispersed or distributed to create the electric field.

Figure 8:
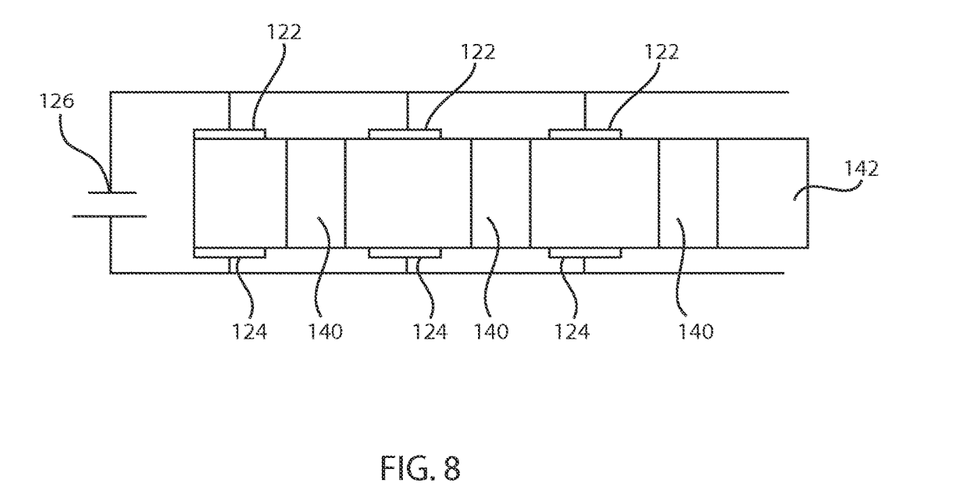
FIG. 8 is a cross-sectional view of a multiple channel sensor in accordance with yet another embodiment.

Referring to FIG. 8, in another embodiment, instead of multiple nanopores 114, multiple channels 140 may be employed.

Figure 9:
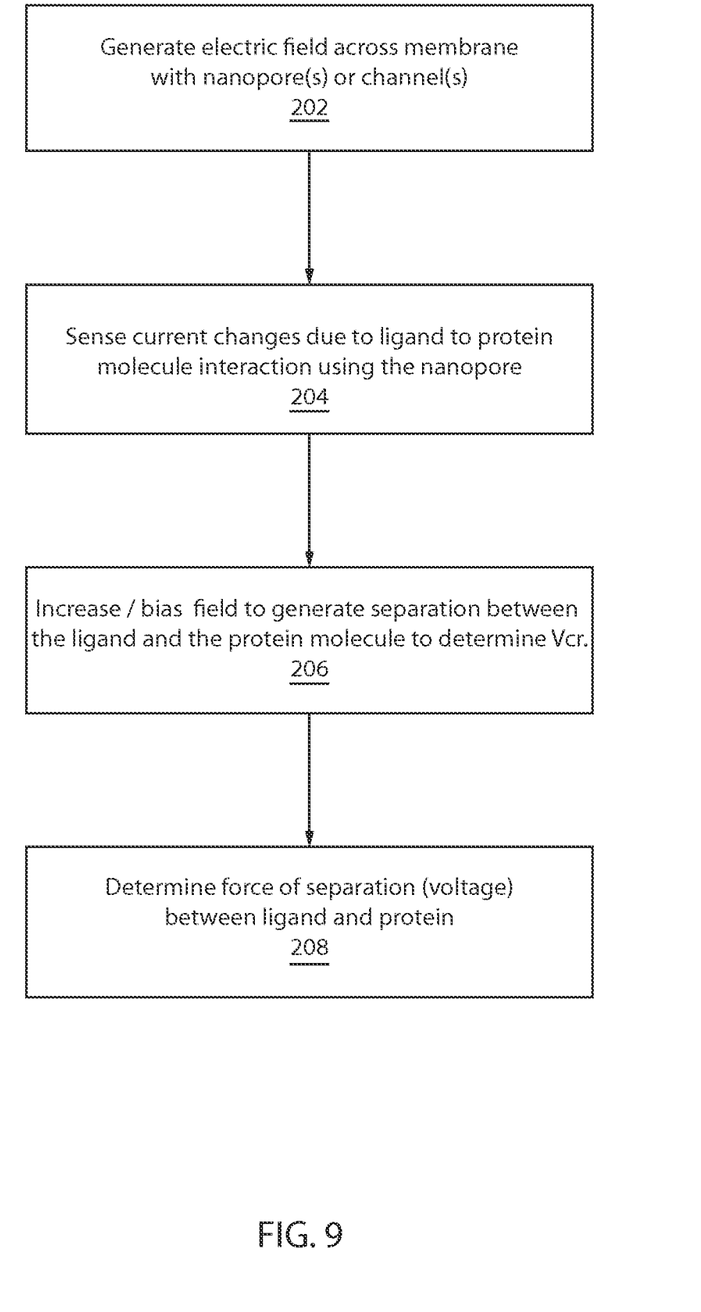
FIG. 9 is a block/flow diagram showing a method for nanosensing in accordance with illustrative embodiments.

Referring to FIG. 9, a method for detecting molecule characteristics is illustratively shown. It should be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems (e.g., circuitry, memory, etc.) that perform the specified functions or acts, or combinations of special purpose hardware and computer instructions.

In block 202, an electric field is generated across a membrane having an opening to drive a charged molecule, e.g., a carbon nanotube, through the opening. The charged molecule may include a closed functionalized end having charged chemical groups therein. The charged molecule (carbon nanotube) is connected to a ligand, and the ligand is bonded to a protein molecule.

The opening may include one or more nanopores or one or more channels. The opening is configured to permit the charged carbon nanotube to pass but to block the protein molecule attached to the carbon nanotube. The opening is filled with an electrolytic solution. In block 204, current changes due to the charged carbon nanotube passing into or through the opening are sensed. The sensing may include measuring current drops and durations to determine a blockage in the opening. Sensing current changes are employed to trigger increasing a biasing value to determine a critical voltage value at which separating occurs between the carbon nanotube and the molecule to infer interaction strength (or affinity).

In block 206, the electric field is biased to cause a separation between the ligand and the protein molecule. In block 208, a voltage at the separation is determined and used to correlate to a characteristic of the protein molecule to ligand interaction. The characteristic may include an affinity between the ligand and the protein molecule. This information may be employed in drug screening applications, or lead optimizations.

Having described preferred embodiments for a nanopore device and method for drug-like molecule screening or lead optimization to a targeted protein (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for detecting a protein molecule characteristics, comprising:
    generating an electric field across a membrane having an opening to drive a charged carbon nanotube molecule through the opening, the charged carbon nanotube being connected to a ligand, the ligand being bonded to the protein molecule, the opening being configured to permit the charged nanotube to pass but to block the protein molecule attached to the charged nanotube, the opening being filled with an electrolytic solution;
    sensing current changes due to the charged carbon nanotube passing into or through the opening;
    biasing the electric field to cause a separation between the ligand and the protein molecule; and
    correlating a voltage at the separation to measure a characteristic of the protein molecule to ligand interaction.

2. The method as recited in claim 1, wherein the opening includes one of a nanopore and a channel.

3. The method as recited in claim 1, wherein sensing includes measuring current drops and durations to determine a blockage in the opening.

4. The method as recited in claim 1, wherein the characteristic includes an affinity between the ligand and the protein molecule.

5. The method as recited in claim 1, wherein the charged carbon nanotube includes a closed functionalized end having charged chemical groups.

6. The method as recited in claim 1, wherein biasing the electric field includes increasing a biasing value to determine a critical voltage value at which separation occurs between the charged carbon nanotube and the protein molecule to infer interaction strength.

7. A method for detecting a protein molecule characteristics, comprising:
- generating an electric field across a membrane having an opening to drive a charged nanowire through the opening, the charged nanowire being connected to a ligand, the ligand being bonded to the protein molecule, the opening being configured to permit the charged nanowire to pass but to block the protein molecule attached to the charged nanowire, the opening being filled with an electrolytic solution;
- sensing current changes due to the charged nanowire passing into or through the opening,
- biasing the electric field to cause a separation between the ligand and the protein molecule; and
- correlating a voltage at the separation to measure a characteristic of the protein molecule to ligand interaction.

* * * * *